United States Patent
Poulson, III et al.

(10) Patent No.: US 8,986,398 B2
(45) Date of Patent: Mar. 24, 2015

(54) HYDRAULIC PROSTHETIC ANKLE

(71) Applicant: Freedom Innovations, LLC, Irvine, CA (US)

(72) Inventors: Arlo Marsh Poulson, III, Salt Lake City, UT (US); Roland Christensen, Fayette, UT (US); Steven Heath, Centerfield, UT (US); Henry Hsu, Aliso Viejo, CA (US)

(73) Assignee: Freedom Innovations, LLC, Irvine, CA (US)

( * ) Notice: Subject to any disclaimer, the term of this patent is extended or adjusted under 35 U.S.C. 154(b) by 89 days.

(21) Appl. No.: 13/793,892

(22) Filed: Mar. 11, 2013

(65) Prior Publication Data

US 2014/0222167 A1     Aug. 7, 2014

Related U.S. Application Data

(60) Provisional application No. 61/761,003, filed on Feb. 5, 2013.

(51) Int. Cl.
   *A61F 2/66*   (2006.01)
   *A61F 2/74*   (2006.01)
   *A61F 2/50*   (2006.01)

(52) U.S. Cl.
   CPC ....... *A61F 2/6607* (2013.01); *A61F 2002/5006* (2013.01); *A61F 2002/5007* (2013.01); *A61F 2002/5035* (2013.01); *A61F 2002/5039* (2013.01); *A61F 2002/5041* (2013.01); *A61F 2002/5073* (2013.01); *A61F 2002/6664* (2013.01); *A61F 2002/6657* (2013.01); *A61F 2002/748* (2013.01); *A61F 2002/5033* (2013.01); *A61F 2002/74* (2013.01); *A61F 2/66* (2013.01); *A61F 2002/745* (2013.01)
   USPC .................................. 623/52; 623/55; 623/26

(58) Field of Classification Search
   USPC ............................. 623/26, 47, 48, 49, 50, 52
   See application file for complete search history.

(56) References Cited

U.S. PATENT DOCUMENTS

| | | | |
|---|---|---|---|
| 2,470,480 | A | 5/1949 | Fogg |
| 2,843,853 | A | 7/1958 | Mauch |
| 3,871,032 | A | 3/1975 | Karas |
| 5,290,319 | A | 3/1994 | Phillips |

(Continued)

FOREIGN PATENT DOCUMENTS

| | | |
|---|---|---|
| DE | 4410730 C1 | 6/1995 |
| EP | 0576379 A1 | 12/1993 |

(Continued)

OTHER PUBLICATIONS

EP Application 14151179.0; filing date Jan. 14, 2014; Freedom Innovations, LLC; European Search Report dated Mar. 21, 2014.

*Primary Examiner* — Marcia Watkins (57) ABSTRACT

A range of motion (ROM) prosthetic foot and passive dampening ankle joint have limited dorsiflexion-plantarflexion (up and down) pivoting to accommodate different environments, and a spring to provide resilient resistance to plantarflexion (or lowering of the toe), and to bias the foot in dorsiflexion (or raising the toe). The ankle joint has a rear pivot rearward of a hydraulic link for a smooth feel. The ankle joint has an internal bumper in a hydraulic cylinder for a smooth feel. The ankle joint has an internal hydraulic compensator disposed in the cylinder and carried by the piston to equalize volume.

23 Claims, 8 Drawing Sheets

(56) References Cited

U.S. PATENT DOCUMENTS

| | | |
|---|---|---|
| 5,810,130 A * | 9/1998 | Mc Candless ........... 188/322.22 |
| 5,921,358 A | 7/1999 | Gramnäs |
| 5,957,981 A | 9/1999 | Gramnäs |
| 6,007,582 A | 12/1999 | May |
| 6,443,993 B1 | 9/2002 | Koniuk |
| 6,855,170 B2 | 2/2005 | Gramnäs |
| 6,875,241 B2 | 4/2005 | Christesen |
| 7,052,519 B1 | 5/2006 | Gramnäs |
| 7,507,259 B2 | 3/2009 | Townsend et al. |
| 7,862,622 B2 | 1/2011 | Dunlap et al. |
| 7,985,265 B2 | 7/2011 | Moser et al. |
| 8,641,780 B2 * | 2/2014 | Abimosleh et al. ............. 623/50 |
| 2006/0235544 A1 | 10/2006 | Iversen et al. |
| 2008/0262635 A1 | 10/2008 | Moser et al. |
| 2008/0281435 A1 * | 11/2008 | Abimosleh et al. ............. 623/50 |
| 2008/0300692 A1 | 12/2008 | Moser et al. |
| 2009/0222105 A1 | 9/2009 | Clausen |
| 2011/0082566 A1 * | 4/2011 | Herr et al. ...................... 623/24 |
| 2011/0307078 A1 * | 12/2011 | Boender ........................ 623/26 |

FOREIGN PATENT DOCUMENTS

| | | |
|---|---|---|
| EP | 1101461 A1 | 5/2001 |
| JP | 59 183747 A * | 10/1984 |
| WO | WO 02/15826 A1 | 2/2002 |
| WO | WO 2011/080556 A2 | 7/2011 |

* cited by examiner

HYDRAULIC PROSTHETIC ANKLE

PRIORITY CLAIM(S)

Priority is claimed to U.S. Provisional Patent Application Ser. No. 61/761,003, filed Feb. 5, 2013, and which is hereby incorporated herein by reference.

BACKGROUND

1. Field of the Invention

The present invention relates generally to prosthetic feet and ankles.

2. Related Art

Prosthetic feet have been developed that utilize composite leaf springs. Such feet, however, may provide difficulties and/or an unnatural gait on slopes or inclined surfaces. Hydraulic ankles have been developed to allow limited range of motion for the foot. For example, see the Mauch Hydraulic Ankle; Endolite Echelon or Elan prosthetic foot. See also U.S. Pat. Nos. 7,985,265; 7,052,519; 6,855,170. Such feet may still provide an unnatural feel.

The improvement and refinement of prosthetics is an ongoing endeavor.

SUMMARY OF THE INVENTION

It has been recognized that it would be advantageous to develop a prosthetic foot that can provide a limited range of motion of the foot about an ankle joint that provides a more natural gait and/or feel.

The invention provides a range of motion (ROM) prosthetic foot and passive dampening ankle joint with limited dorsiflexion-plantarflexion (up and down) pivoting to accommodate different environments, and a spring to provide resilient resistance to plantarflexion (or lowering of the toe), and to bias the foot in dorsiflexion (or raising the toe). The ankle joint has a rear pivot rearward of a hydraulic link for a smooth feel. The ankle joint has an internal bumper in a hydraulic cylinder for a smooth feel. The ankle joint has an internal hydraulic compensator disposed in the cylinder and carried by the piston to equalize volume.

The invention provides a prosthetic foot with an attachment configured to be coupled to a socket or pylon attached to a remnant limb of an amputee. A prosthetic foot is coupled to the attachment and includes a toe end at a toe location of a natural foot, and a heel end at a heel location of a natural foot. A passive dampening ankle joint is coupled between the attachment and the prosthetic foot to provide limited dorsiflexion-plantarflexion (up and down) pivoting of the foot with respect to the attachment about a horizontal medial-lateral (lateral side-to-side) pivot axis. The ankle joint includes an ankle platform attached to the foot and a body with a cylinder rigidly attached to the attachment and pivotally coupled to the ankle platform at the pivot axis. A piston is reciprocally disposed in the cylinder. A link is pivotally coupled to and between the piston and the ankle platform. The pivot axis is disposed rearwardly with respect to the link and the link is disposed forwardly of the pivot axis.

BRIEF DESCRIPTION OF THE DRAWINGS

Additional features and advantages of the invention will be apparent from the detailed description which follows, taken in conjunction with the accompanying drawings, which together illustrate, by way of example, features of the invention; and, wherein.

Reference will now be made to the exemplary embodiments illustrated, and specific language will be used herein to describe the same. It will nevertheless be understood that no limitation of the scope of the invention is thereby intended.

DETAILED DESCRIPTION OF EXAMPLE EMBODIMENT(S)

As illustrated in FIGS. 1-14, a range of motion (ROM) prosthetic foot, indicated generally at 10, with a passive dampening ankle joint, indicated generally at 14, in an example implementation in accordance with the invention is shown. The (ROM) prosthetic foot 10 and the passive dampening ankle joint 14 can have limited dorsiflexion-plantarflexion (up and down) pivoting to accommodate different environments, such as inclined terrain, by allowing a foot or foot keel 18 to pivot about a horizontal medial-lateral (lateral side-to-side) pivot axis 22 to accommodate the incline. For example, the foot keel 18 can pivot in plantarflexion (toe pivoting downwardly) when a downward slope is encountered; or the foot keel 18 can pivot in dorsiflexion (toe pivoting upwardly) when an upward slop is encountered.

The ankle joint 14 of the ROM foot 10 is affixed to a prosthetic foot or a foot keel 18, and has a standard fixture or attachment 26 to allow attachment to a pylon or socket to receive a remnant limb of an amputee. Thus, the prosthetic foot or foot keel 18 is coupled to the attachment 26. The prosthetic foot 10 or foot keel 18 can include an elongated forefoot keel 30 and an elongated footplate 34 coupled to the forefoot keel. The forefoot keel 30 can extend between a toe location 38 of a natural foot and near a heel location 42 of a natural foot. The footplate 34 can be coupled to the forefoot keel 30 at the toe location 38, such as with a composite wrap wrapping the distal ends of the forefoot keel and footplate. The footplate 34 can extend between the toe location 38 and the heel location 42. The foot keel 18, or the forefoot keel 30 and the footplate 34, can be formed of a composite material, namely carbon fiber in a resin matrix. The foot keel 18, or the forefoot keel 30 and the footplate 34, can form springs, such as leaf springs, that are resilient and bendable or compressible under load to store energy in the springs when deflected, and return the energy from the springs when released. For example, at heel strike, the foot keel 18 can bend to store energy that is returned or released during toe-off. In addition, the foot keel, or the forefoot keel and/or the footplate, can be bifurcated wholly or partially to adjust for or accommodate uneven terrain. As shown, the forefoot keel and the footplate are partially bifurcated from the toe location through an arch location.

The ankle joint 14 is coupled between the attachment 26 and the prosthetic foot or foot keel 18, or forefoot keel 30. The ankle joint 14 dampens the limited pivoting of the foot keel 18 in the dorsiflexion-plantarflexion (up and down) direction, and also biases the foot keel 18 to pivot in a dorsiflexion (toe up) direction, and thus resists the foot keel from pivoting in a plantarflexion (toe down) direction, to provide a more natural action of the foot/ankle. For example, when at rest or not in use, the foot keel 18 is drawn to a more natural position, i.e. toe up, to resist settling to a downward position that can become inadvertently snagged upon sudden use.

The ankle joint 14 has an upper housing or body 50 pivotally coupled to a lower base or ankle platform 54 at the pivot axis 22. The base or ankle platform 54 can be attached or affixed to the foot keel 18 or forefoot keel 30, while the body 50 is affixed or rigidly attached to the attachment 26, and thus the pylon or socket. For example, the ankle platform 54 can be rigidly affixed to a proximal end of the forefoot keel 30. The attachment 26 can be rigidly mounted on the housing or body 50. The attachment can form a cap or top cover to the body. A cover portion can be integrally formed together with the attachment and can cover the body or be flush therewith.

The body 50 can be pivotally attached to the ankle platform 54 by an ankle pin, which can define the pivot axis 22. The pivotal attachment can include associated bushings and/or bearings. The pivot axis 22 is located at a rear of the housing or body 50, and/or at a rear of the base or ankle platform 54. The body 50 can have a rear lobe 58 extending downward from the body at a rear of the body. The pivot axis 22 can be located in a bottom of the lobe. The lobe 58 and ankle pin or pivot axis can be received in a slot or cavity 62 in the ankle platform 54. The ankle pin can extend through the ankle platform, slot and lobe of the body.

Figure 1:
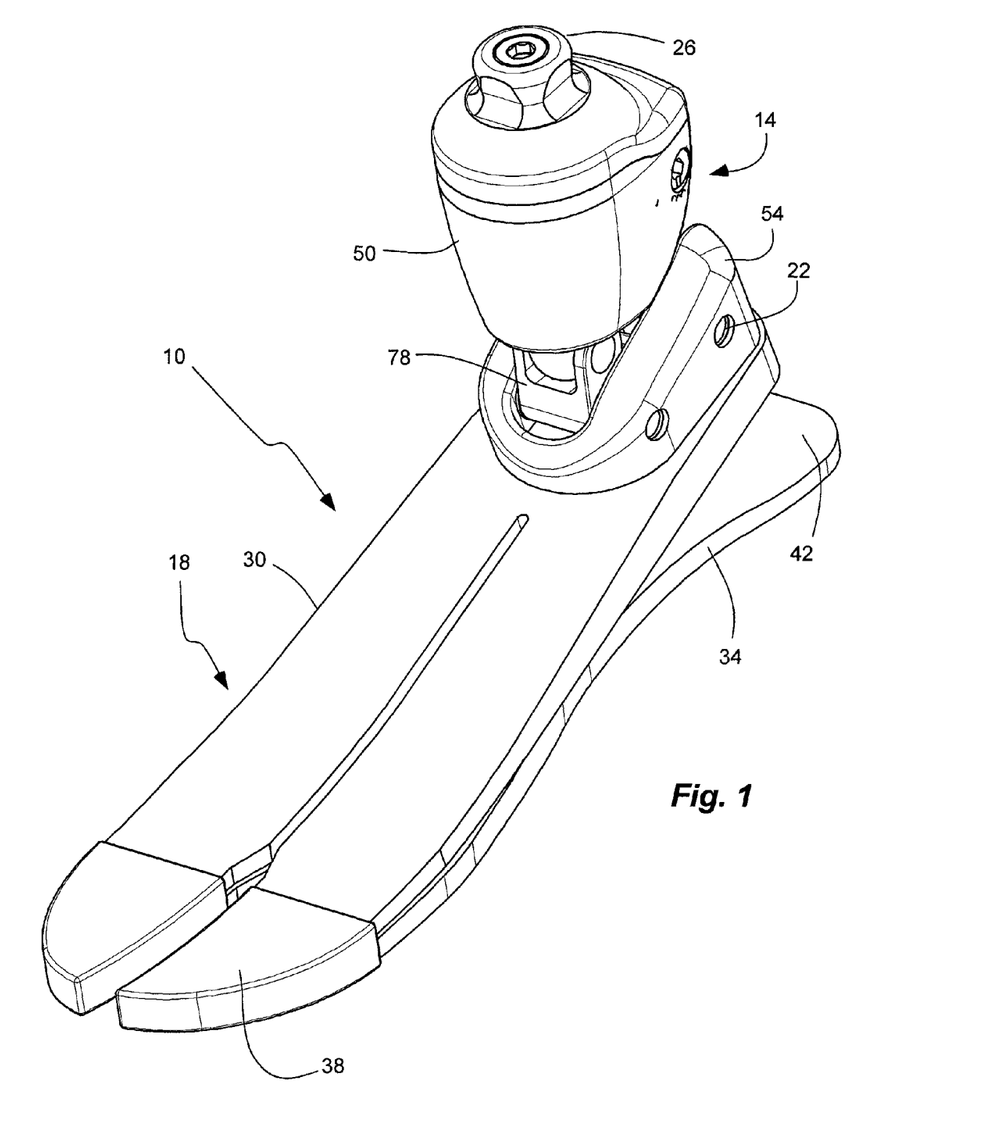
FIG. 1 is a perspective view of a prosthetic foot with a passive dampening ankle joint in accordance with an embodiment of the present invention.
Figures 2, 4:
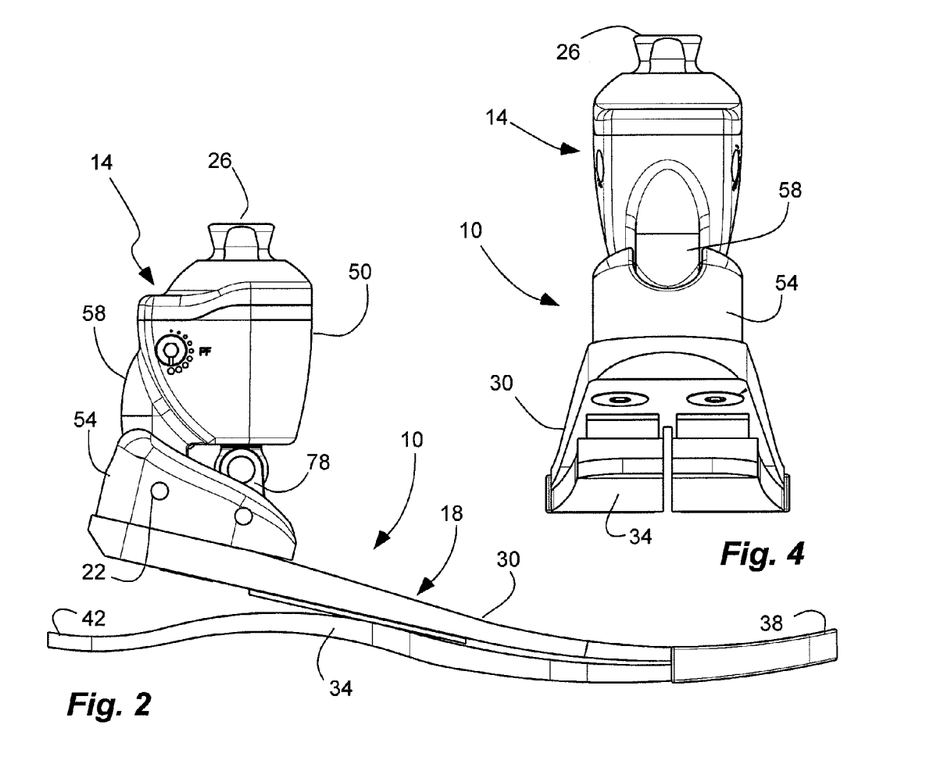
FIG. 2 is a side view of the prosthetic foot of FIG. 1.
FIG. 4 is a rear view of the prosthetic foot of FIG. 1.
Figure 3:
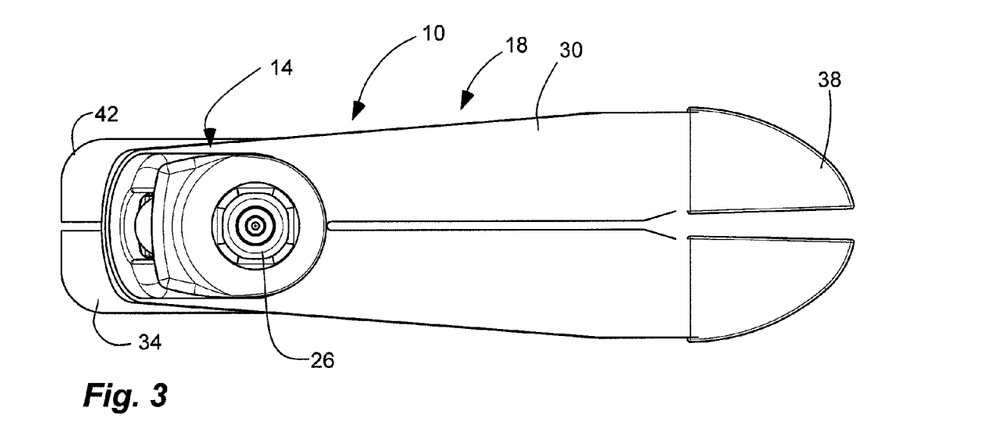
FIG. 3 is a top view of the prosthetic foot of FIG. 1.
Figure 5A:
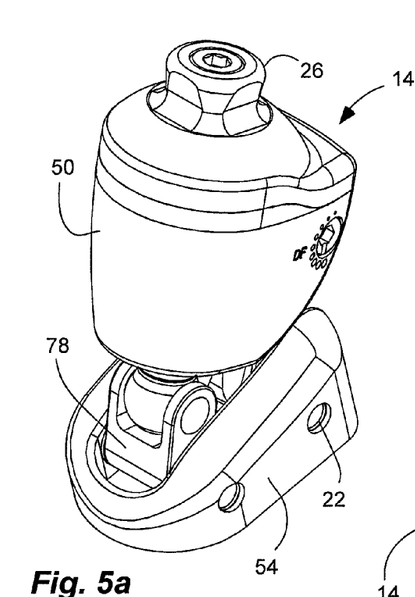
FIG. 5a is a top perspective view of the passive dampening ankle joint of FIG. 1.
Figure 5B:
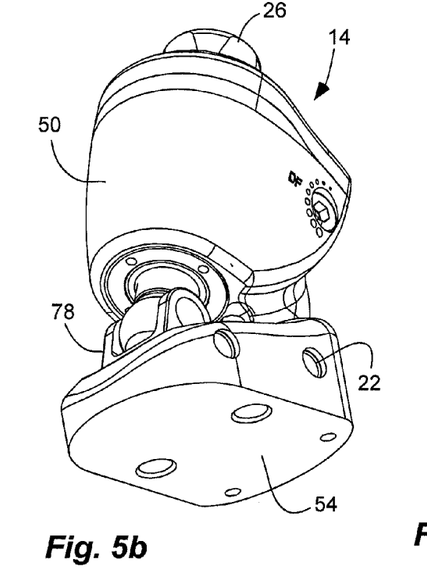
FIG. 5b is a bottom perspective view of the passive dampening ankle joint of FIG. 1.
Figure 6:
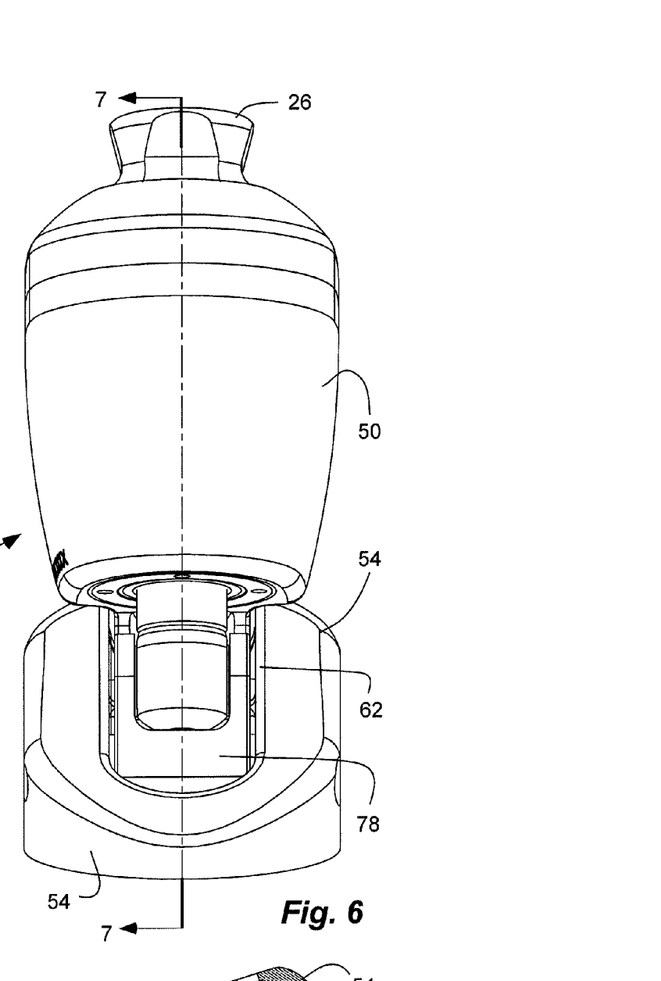
FIG. 6 is a front view of the passive dampening ankle joint of FIG. 1.
Figure 7:
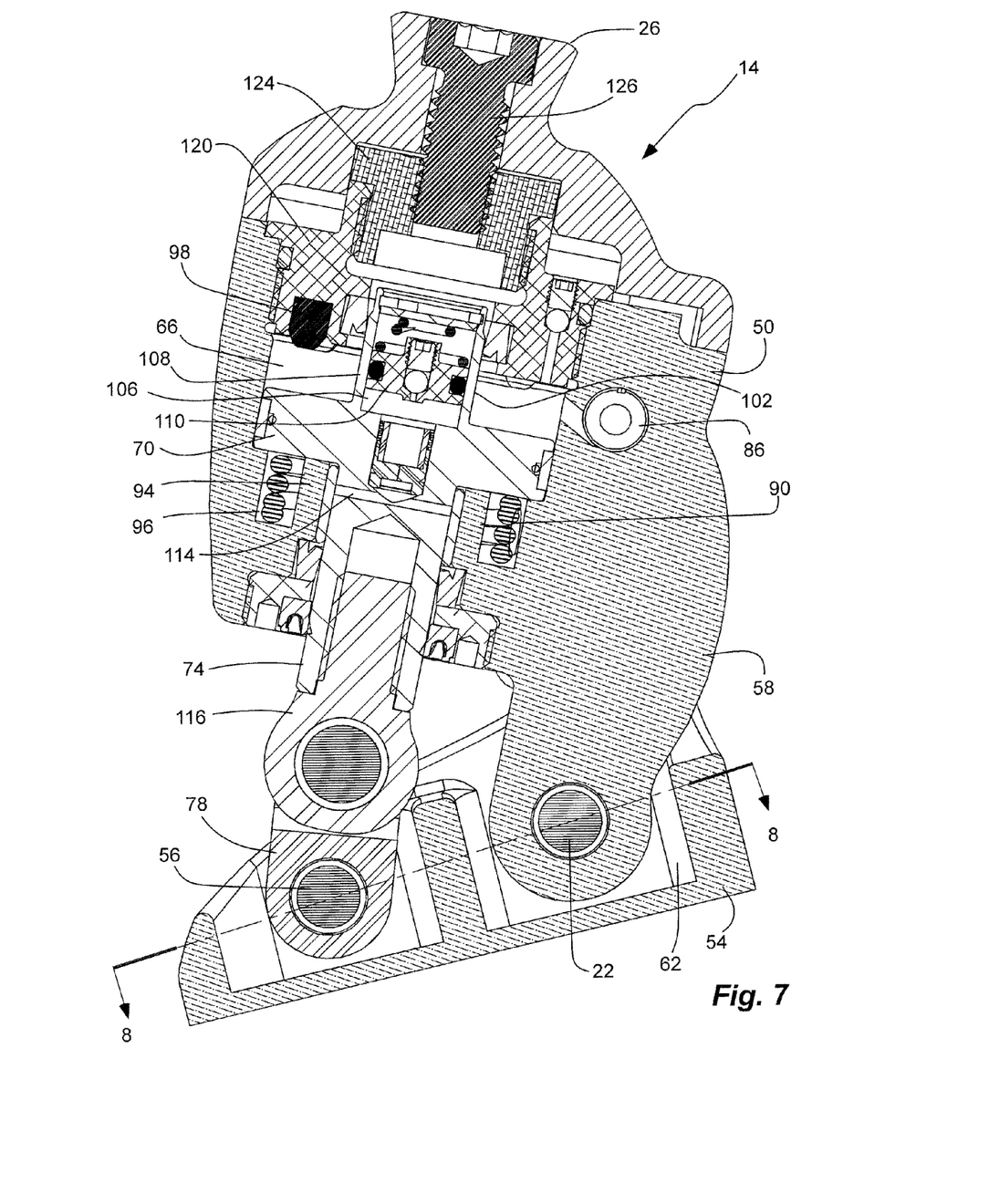
FIG. 7 is a cross-sectional side view of the passive dampening ankle joint of FIG. 1 taken along line 7 of FIG. 6.
Figure 8:
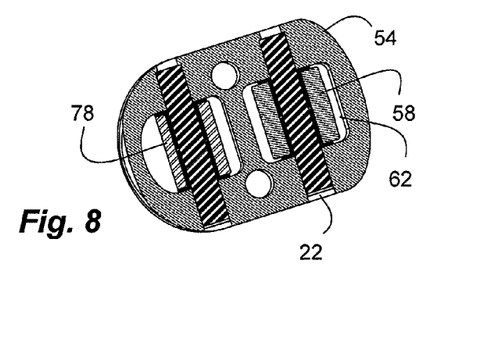
FIG. 8 is a cross-sectional top view of a portion of the passive dampening ankle joint of FIG. 1 taken along line 8 of FIG. 7.
Figure 9:
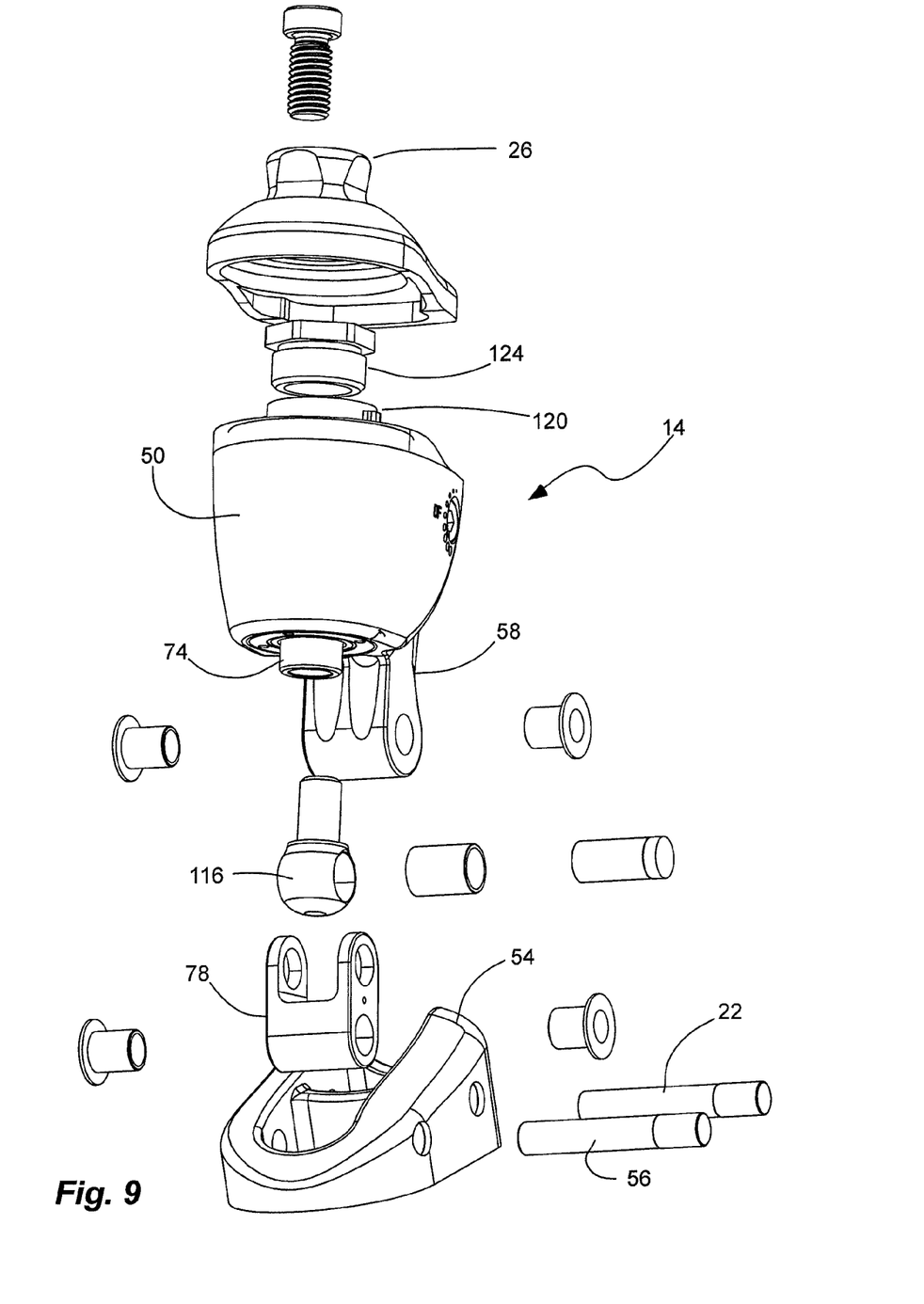
FIG. 9 is an exploded view of the passive dampening ankle joint of FIG. 1.
Figure 10:
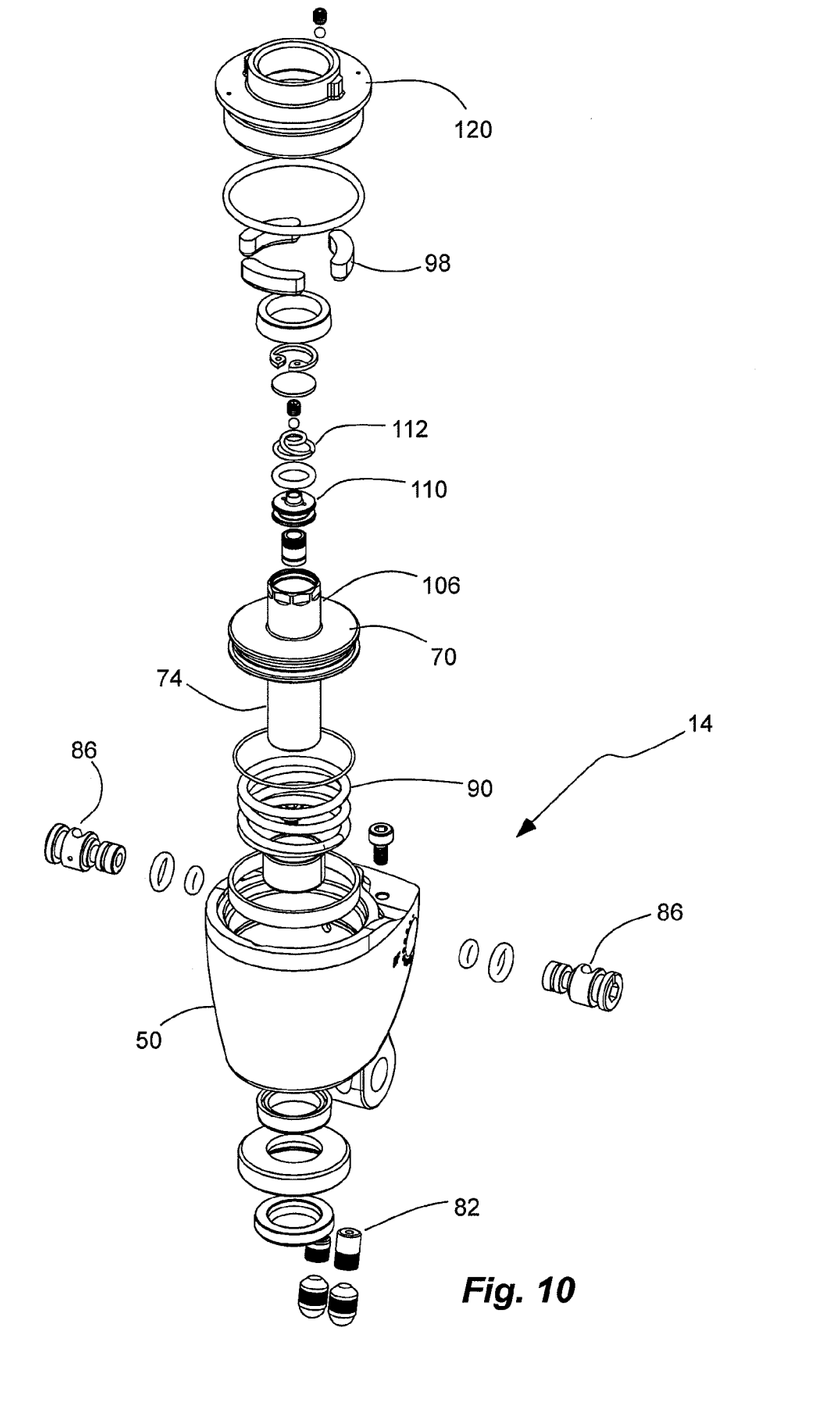
FIG. 10 is an exploded view of a housing an internal components of the passive dampening ankle joint of FIG. 1.
Figure 11A:
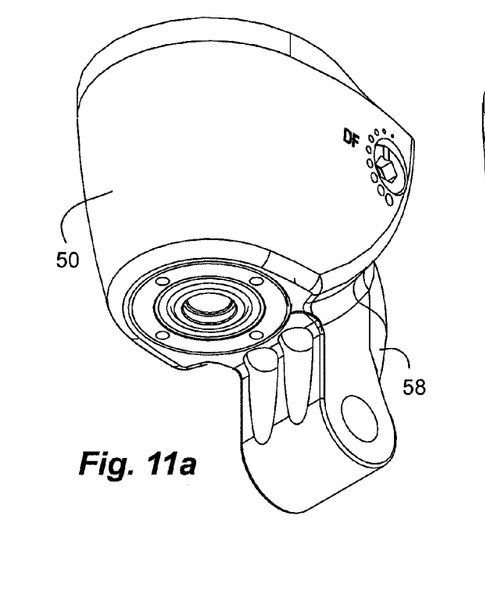
FIG. 11a is a bottom perspective view of the housing of the passive dampening ankle joint of FIG. 1.
Figure 11B:
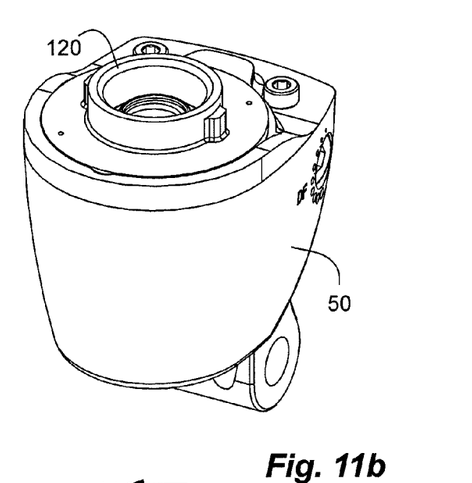
FIG. 11b is a top perspective view of the housing of the passive dampening ankle joint of FIG. 1.
Figure 12:
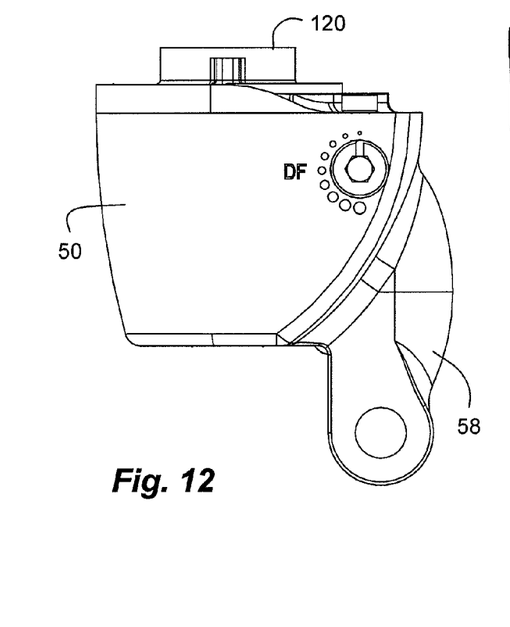
FIG. 12 is a side view of the housing of the passive dampening ankle joint of FIG. 1.
Figure 13:
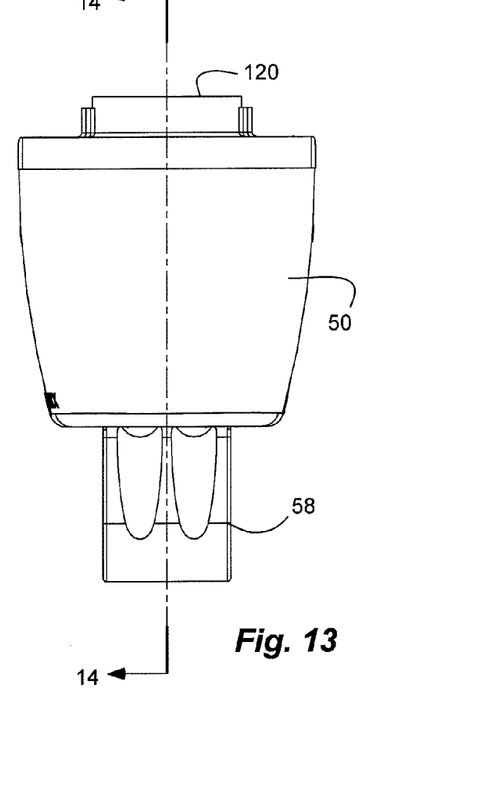
FIG. 13 is a front view of the housing of the passive dampening ankle joint of FIG. 1.
Figure 14:
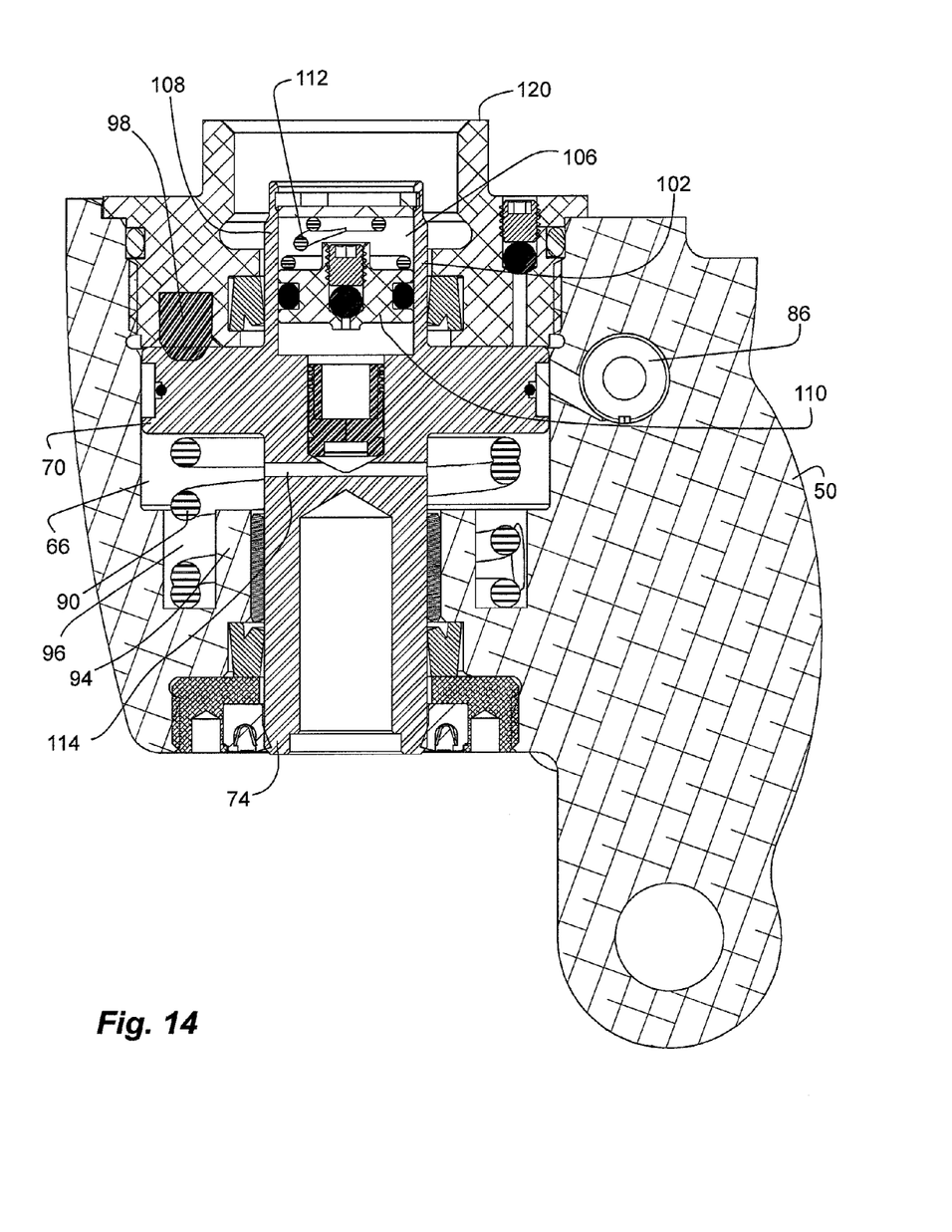
FIG. 14 is a cross-sectional side view of the housing and the internal components of the passive dampening ankle joint of FIG. 1 taken along line 14 of FIG. 13.

The ankle joint 14 includes a hydraulic piston/cylinder that is disposed in the housing or body 50, and coupled to the base or ankle platform 54, to dampen pivotal movement between the housing and the base, or between the body and ankle platform, and thus between the foot keel and the leg (or attachment). A hollow or cylinder 66 is defined in the housing 50. A piston 70 is movably received and reciprocally received in the cylinder 66, and separates the cylinder into a pair of opposite chambers on opposite sides of the piston. A rod 74 is coupled to the piston, and extends out of the housing or body 50 to be coupled to the base or ankle platform 54 by a clevis 78. The clevis 78 can be pivotally coupled to the piston or rod 74 thereof and the ankle platform 54 by pins and associated bushings or bearings. The clevis 78 allows the piston 70 to move linearly in the cylinder 66 even though the housing or body 50 is pivotally coupled to the base or ankle platform 54. In addition, the clevis 78 reduces wear on the piston and cylinder by keeping side loads off the piston rod. The clevis 78 can define a link pivotally coupled between the piston 70 or rod 74 and the ankle platform 54. The pivot axis 22 is disposed rearwardly with respect to the link or clevis 78, and the link or clevis 78 is disposed forwardly of the pivot axis 22. The pivot axis 22 is disposed at a rear of the ankle platform 54 and body 50 nearer a rear of the foot than the link or clevis 78; and the link or clevis 78 can be pivotally coupled at a front of the ankle platform 54 forward of the pivot axis 22. Thus, the foot 10 and the ankle joint 14 provide a rear pivot behind the link or clevis 78 that is believed and been found to provide a smoother feel with respect to a forward pivot, even though the rear pivot results in non-bio mimicry. The pivot axis 22 can be located rearward of an ankle location of a natural foot. An axis of the attachment 26, the link (or clevis 78) and a pivot axis 56 of the link (or clevis 78) to the ankle platform 54 can be substantially aligned, with the attachment 26 and the piston 70 being disposed over the link or clevis 78, as shown in FIG. 7. The link or clevis 78 can extend into a slot or cavity of the ankle platform.

Also formed in the housing or body 50 are hydraulic fluid passages, such as a pair of flow channels extending between the pair of chambers. For example, an upward passage can extend from a lower to an upper chamber, and a downward passage can extend from the upper to the lower chamber. A pair of unidirectional check valves 82 (FIG. 10) is disposed in the fluid passages, each disposed in a different one of the pair of flow channels to allow flow in only one direction. Thus, as the piston 70 moves in the cylinder 66, hydraulic fluid is displaced from one side of the piston to the other, or between the chambers, upward through the upward passage, and downward through the downward passage. In addition, a pair of control valves 86 is also disposed in the fluid passages, each disposed in a different one of the pair of flow channels to vary the resistance to flow of the hydraulic fluid. The control valves 86 can vary the size of an orifice through which the hydraulic fluid passes. In one aspect, the control valves can be infinitely adjustable between two extremes, as opposed to being discreetly adjustable at predefined orifice sizes between two extremes. Thus, the control valves can continuously vary the size of the orifice. In one aspect, the control valves only control the size of the orifice, without completely closing the orifice. Thus, the piston can always be free to move, and the foot keel can always be free to pivot.

In addition, a biasing member such as a compressible coil spring 90 can be disposed in one of the chambers, such as the lower chamber, to bear against the piston 70 to bias the piston. The spring 90 can provide resilient resistance to plantarflexion (or lowering of the toe), and to bias the foot in dorsiflexion (or raising the toe). Thus, the spring 90 can raise the piston 70 and draw it further into the cylinder 66, to raise the foot keel 18. A bottom of the cylinder 66 can include an annular flange 94 extending from a bottom of the cylinder or body into the cylinder to form an annular groove 96. When the piston 70 is drawn downwardly, the spring 90 is compressed into the annular groove 96. In addition, the annular flange 94 can provide linear stability to the rod 74, and thus the piston 70.

In addition, a bumper 98 can be disposed at an end of the cylinder 66 in one of the chambers, such as the upper chamber, that can abut to the piston 70 at an end of a stroke of the piston. The bumper can include a plurality of arcuate bumpers circumscribing an axis of the cylinder to balance force on the piston as it abuts the bumpers. The spring 90 can bias the piston 70 against or towards the bumper 98. The bumper 98 cushions the force of the piston against the cylinder or top thereof at the end of the stroke of the piston to provide a more comfortable feel.

Furthermore, the ankle joint can include a hydraulic compensator 102 carried by the piston 70. The piston 70 can be a primary piston, and the cylinder 66 can be a primary cylinder.

The hydraulic compensator 102 can include a secondary cylinder 106 disposed in the housing or body or cylinder 66 thereof, and fluidly coupled to at least one of the chambers. The secondary chamber 106 can be disposed in the primary piston 70 opposite the rod 74. A shaft 108 can extend from the piston 70 opposite the rod 74. The secondary chamber 106 can be formed in the shaft 108. The shaft 108 and the rod 74 can be integrally formed at the same time with the piston 70. A secondary piston 110 can be slidably disposed in the secondary cylinder 106. Thus, the secondary piston 110 can be carried by the primary piston 70 as well. A secondary channel 114 can be fluidly coupled to the secondary cylinder 106 and disposed in the primary piston 70. The hydraulic compensator 102 can have a very small orifice, and thus can cycle very slowly. The secondary or compensating piston 110 can cycle independently of the primary piston 70. Thus, the hydraulic compensator 102 can adjust for oil lose and/or temperature changes. A secondary spring 112 can bias the secondary piston 110 to a closed or lower volume of the secondary cylinder 106. The hydraulic compensator 102 can have a shaft 108 in which the secondary cylinder 106 is formed and in which the secondary piston 110 is carried. The shaft 108 can be the same diameter as the rod 74 on the opposite side of the piston, and can extend through the primary cylinder opposite the rod, to create substantially equal volumes in the chambers on opposite sides of the primary piston. Thus, the primary piston and primary cylinder do not require a compensator or overflow reservoir due to unequal volumes.

The rod 74 of the primary piston 70 can include a portion formed integrally with the piston, and a plunger eyebolt 116 fastened to the rod 74 and pivotally coupled to the ankle platform 54. Thus, the clevis 78 and the eyebolt 116 can be removed and replaced if necessary without disturbing the hydraulic piston/cylinder.

The cylinder 66 can be formed in the body 50, and closed or capped by an annular top cap 120. The annular top cap 120 can be coupled to the body 50 with the cylinder 66 defined in the body 50 and closed by the top cap. The top cap 120 can be annular to receive the hydraulic accumulator 102 therein during stroking of the primary piston 70. As described above, the hydraulic compensator 102 can be carried by the piston 70, and disposed in the shaft 108 coupled to the piston and displaceable in the annular top cap 120 as the piston moves. The top cap 120 can be closed or capped by a top cap thread plug 124, which can both close the top cap, and receive a bolt or fastener 126 to secure the attachment 26 to the body 50. The top cap thread plug 124, and the bolt 126 and attachment 26, can be removed to allow access to the hydraulic compensator 102, or top cap 120. The secondary or compensator piston 110 can have a bore therein closed by a plug to allow the addition and/or removal of hydraulic fluid. In another aspect, the cop cap can have a bore therein closed by a plug to allow the addition and/or removal of hydraulic fluid. The secondary cylinder 106 can be closed by a plate and a C-clip.

The check valves 82 can be inserted in through a bottom of the body, adjacent the lobe, and held and/or sealed in by plugs. The control valves 86 can be disposed on the lateral sides of the body, and on opposite sides from one another.

During gait, the ankle joint 14 of the ROM foot 10 acts as follows:

on heel strike, the foot keel 18 (and forefoot keel 30) moves in plantar flexion (toe lowers)—against the spring force of spring 90 and pulling the piston 70 down, thus displacing hydraulic fluid through the upward passage from the lower chamber to the upper chamber.

at mid-stance, the foot keel moves in dorsiflexion (toe pivoting upwardly)—driving the piston upward and displacing the hydraulic fluid through the downward passage from the upper chamber to the lower chamber.

at toe-off, the foot keel moves in dorsiflexion (toe pivoted upward)—driving the piston upward and displacing hydraulic fluid through the downward passage from the upper chamber to the lower chamber.

during swing phase, the spring pushes the piston upward (or maintaining the piston upward), drawing the foot keel in dorsiflexion (toe pivoted upward).

All movement of the foot keel can be dampened, or resisted, by the hydraulic piston/cylinder, with the orifices in the control valves resisting movement of the fluid, and thus movement of the piston, and thus movement of the foot keel.

In addition, at rest, the spring 90 draws the foot keel into dorsiflexion (toe up). The spring 90 maintains the toe of the foot keel up during swing phase, and/or during rest. The spring 90 can always be under compression. Thus, when not in use, the foot keel is drawn to a more natural position, and resists settling to a downward position that can become inadvertently snagged upon sudden use.

In one aspect, the hydraulic piston/cylinder may not have on/off valves, i.e. the control valves may not close, and thus the ankle joint may not adjust the angle of the foot keel with respect to the leg or pylon at any fixed angle.

In another aspect, the ankle joint can be passive, and not dynamic, in that is may not control electronics or sensors, and may not dynamically adjust during use.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

The invention claimed is:

1. A prosthetic foot device, comprising:
   a) an attachment configured to be coupled to a socket or pylon attached to a remnant limb of an amputee;
   b) a prosthetic foot coupled to the attachment and including a toe end at a toe location of a natural foot, and a heel end at a heel location of the natural foot;
   c) a passive dampening ankle joint coupled between the attachment and the prosthetic foot to provide limited dorsiflexion-plantarflexion pivoting of the foot with respect to the attachment about a horizontal medial-lateral pivot axis, the ankle joint including:
      i) an ankle platform attached to the foot;
      ii) a body with a cylinder rigidly attached to the attachment and pivotally coupled to the ankle platform at the pivot axis;
      iii) a piston reciprocally disposed in the cylinder and dividing the cylinder into upper and lower chambers;
      iv) a link pivotally coupled to and between the piston and the ankle platform; and
      v) a spring disposed in the lower chamber and bearing against the piston to raise the piston, and thus the foot during swing phase, and to provide resilient resistance to plantarflexion during heel strike; and
   d) the pivot axis being disposed rearwardly with respect to the link and the link being disposed forwardly of the pivot axis.

2. A passive dampening ankle joint device coupled between an attachment and a prosthetic foot to provide limited dorsiflexion-plantarflexion pivoting of the foot with respect to the attachment about a horizontal medial-lateral pivot axis, the passive dampening ankle joint comprising:

a) an ankle platform attached to the foot;
b) a body with a cylinder rigidly attached to the attachment and pivotally coupled to the ankle platform at the pivot axis;
c) a piston reciprocally disposed in the cylinder and dividing the cylinder into a pair of chambers, including upper and lower chambers;
d) a spring always under compression and disposed in the lower chambers and bearing against the piston to raise the piston, and thus the foot during swing phase, and to provide resilient resistance to plantarflexion during heel strike;
e) a pair of flow channels extending between the pair of chambers;
f) a pair of check valves each disposed in a different one of the pair of flow channels configured to allow hydraulic fluid to flow from one chamber to another chamber through one channel, and from the another chamber to the one chamber through another channel;
g) a pair of control valves each disposed in a different one of the pair of flow channels configured to vary resistance to flow of the hydraulic fluid;
h) a link pivotally coupled to and between the piston and the ankle platform; and
i) the pivot axis being disposed rearwardly with respect to the link and the link being disposed forwardly of the pivot axis.

3. A device in accordance with claim 2, wherein the pivot axis is disposed at a rear of the ankle platform; and wherein the link is pivotally coupled at a front of the ankle platform.

4. A device in accordance with claim 2, further comprising:
a rear lobe extending downward from the body at a rear of the body; and
the pivot axis being located in a bottom of the lobe; and
the rear lobe received in a slot in the ankle platform.

5. A device in accordance with claim 2, wherein the piston is a primary piston and the cylinder is a primary cylinder; and further comprising a hydraulic compensator to adjust for hydraulic fluid loss or temperature change or both, including:
a) a secondary cylinder disposed in a housing and fluidly coupled to at least one of the chambers;
b) a secondary piston slidably disposed in the secondary cylinder;
c) a secondary spring biasing the secondary piston to a lower volume of the secondary cylinder; and
d) a small orifice such that the secondary piston cycles independently of the primary piston.

6. A device in accordance with claim 5, wherein the compensator further comprises:
a) the secondary chamber being disposed in the primary piston and the secondary piston being carried by the primary piston; and
b) a secondary channel fluidly coupled to the secondary cylinder and disposed in the primary piston.

7. A device in accordance with claim 2, further comprising:
an annular top cap coupled to the body with the cylinder defined in the body and closed by the top cap; and
a plurality of arcuate bumpers carried by the top cap and disposed at an end of the upper chamber and circumscribing an axis of the cylinder and abutting to the piston at an end of a stroke of the piston.

8. A device in accordance with claim 2, further comprising:
a rod coupled to the piston and extending out of the body and pivotally coupled to the link;
an annular top cap coupled to the body with the cylinder defined in the body and closed by the top cap;
a shaft coupled to the piston opposite the rod and extending through the annular top cap; and
a hydraulic compensator carried by the piston and disposed in the shaft coupled to the piston and displaceable in the annular top cap as the piston moves.

9. A device in accordance with claim 8, further comprising:
a plug disposed in the annular top cap; and
a fastener coupling the attachment to the plug, and thus the body.

10. A device in accordance with claim 2, further comprising:
an annular groove in a bottom of the cylinder with the spring compressed into the annular groove when the piston is drawn downwardly.

11. A device in accordance with claim 2, further comprising:
a rod coupled to the piston and extending out of the body;
an eyebolt fastened to the rod; and
a clevis pivotally coupled to the eyebolt and the ankle platform, and defining the link, to allow the piston to move linearly in the cylinder with the body pivotally coupled to the ankle platform.

12. A device in accordance with claim 2, wherein each of the pair of control valves comprises a variable size orifice through which the hydraulic fluid passes, and a respective control valve varies the size of the variable size orifice to vary resistance to flow of the hydraulic fluid.

13. A prosthetic foot device, comprising:
a) an attachment configured to be coupled to a socket or pylori attached to a remnant limb of an amputee;
b) a prosthetic foot coupled to the attachment and including an elongated forefoot keel extending between a toe location of a natural foot and near a heel location of the natural foot, and an elongated footplate coupled to the forefoot keel at the toe location and extending between the toe location and the heel location, the forefoot keel and the footplate being formed of a composite material with fiber in a resin matrix and forming springs that are resilient and bendable to store energy in the springs when deflected and return the energy from the springs when released;
c) a passive dampening ankle joint coupled between the attachment and the prosthetic foot to provide limited dorsiflexion-plantarflexion pivoting of the foot with respect to the attachment about a horizontal medial-lateral pivot axis, the ankle joint including:
i) an ankle platform attached to the foot;
ii) a body with a cylinder rigidly attached to the attachment and pivotally coupled to the ankle platform at the pivot axis;
iii) a piston reciprocally disposed in the cylinder and dividing the cylinder into a pair of chambers, including upper and lower chambers;
iv) a pair of flow channels extending between the pair of chambers;
v) a pair of check valves each disposed in a different one of the pair of flow channels configured to allow hydraulic fluid to flow from one chamber to another chamber through one channel, and from the another chamber to the one chamber through another channel;
vi) a pair of control valves each disposed in a different one of the pair of flow channels configured to vary resistance to flow of the hydraulic fluid; and
vii) a link pivotally coupled to and between the piston and the ankle platform; and
viii) a spring always under compression and disposed in the lower chamber and bearing against the piston to raise the piston, and thus the forefoot keel during swing phase, and to provide resilient resistance to plantarflexion during heel strike;

d) the pivot axis being disposed rearwardly with respect to the link and the link being disposed forwardly of the pivot axis.

14. A device in accordance with claim 13, wherein the pivot axis is disposed at a rear of the ankle platform nearer a rear of the foot than the link; and wherein the link is pivotally coupled at a front of the ankle platform.

15. A device in accordance with claim 13, further comprising:
  a rear lobe extending downward from the body at a rear of the body; and
  the pivot axis being located in a bottom of the lobe; and
  the rear lobe received in a slot in the ankle platform.

16. A device in accordance with claim 13, wherein the piston is a primary piston and the cylinder is a primary cylinder; and further comprising a hydraulic compensator to adjust for hydraulic fluid loss or temperature change, or both, including:
  a) a secondary cylinder disposed in a housing and fluidly coupled to at least one of the chambers;
  b) a secondary piston slidably disposed in the secondary cylinder;
  c) a secondary spring biasing the secondary piston to a lower volume of the secondary cylinder; and
  d) a small orifice such that the secondary piston cycles independently of the primary piston.

17. A device in accordance with claim 16, wherein the compensator further comprises:
  a) the secondary chamber being disposed in the primary piston and the secondary piston being carried by the primary piston; and
  b) a secondary channel fluidly coupled to the secondary cylinder and disposed in the primary piston.

18. A device in accordance with claim 13, further comprising:
  an annular top cap coupled to the body with the cylinder defined in the body and closed by the top cap; and
  a plurality of arcuate bumpers carried by the annular top cap and disposed at an end of the upper chamber and circumscribing an axis of the cylinder and abutting to the piston at an end of a stroke of the piston.

19. A device in accordance with claim 13, further comprising:
  a rod coupled to the piston and extending out of the body and pivotally coupled to the link;
  an annular top cap coupled to the body with the cylinder defined in the body and closed by the top cap;
  a shaft coupled to the piston opposite the rod and extending through the annular top cap; and
  a hydraulic compensator carried by the piston and disposed in the shaft coupled to the piston and displaceable in the annular top cap as the piston moves.

20. A device in accordance with claim 19, further comprising:
  a plug disposed in the annular top cap; and
  a fastener coupling the attachment to the plug, and thus the body.

21. A device in accordance with claim 13, further comprising:
  an annular groove in a bottom of the cylinder with the spring compressed into the annular groove when the piston is drawn downwardly.

22. A device in accordance with claim 13, further comprising:
  a rod coupled to the piston and extending out of the body;
  an eyebolt fastened to the rod; and
  a clevis pivotally coupled to the eyebolt and the ankle platform, and defining the link, to allow the piston to move linearly in the cylinder with the body pivotally coupled to the ankle platform.

23. A device in accordance with claim 13, wherein each of the pair of control valves comprises a variable size orifice through which the hydraulic fluid passes, and a respective control valve varies the size of the variable size orifice to vary resistance to flow of the hydraulic fluid.

* * * * *